(12) United States Patent
Nazzaro et al.

(10) Patent No.: US 11,241,532 B2
(45) Date of Patent: Feb. 8, 2022

(54) DRUG DELIVERY SYSTEM WITH SENSOR HAVING OPTIMIZED COMMUNICATION AND INFUSION SITE

(71) Applicant: Insulet Corporation, Acton, MA (US)

(72) Inventors: David Nazzaro, Groveland, MA (US); John D'Arco, Wilmington, MA (US); Jason O'Connor, Acton, MA (US); Ian McLaughlin, Boxboro, MA (US)

(73) Assignee: INSULET CORPORATION, Acton, MA (US)

( * ) Notice: Subject to any disclaimer, the term of this patent is extended or adjusted under 35 U.S.C. 154(b) by 655 days.

(21) Appl. No.: 16/116,071

(22) Filed: Aug. 29, 2018

(65) Prior Publication Data
US 2020/0069875 A1 Mar. 5, 2020

(51) Int. Cl.
*A61M 5/168* (2006.01)
*A61B 5/145* (2006.01)
(Continued)

(52) U.S. Cl.
CPC ..... *A61M 5/16836* (2013.01); *A61B 5/14532* (2013.01); *A61M 5/14244* (2013.01);
(Continued)

(58) Field of Classification Search
CPC . A61B 5/14532; A61B 5/4839; A61B 5/6849; A61M 2005/14268;
(Continued)

(56) References Cited

U.S. PATENT DOCUMENTS 441,663 A 12/1890 Hofbauer
955,911 A 4/1910 Saegmuller
(Continued)

FOREIGN PATENT DOCUMENTS

CA 2863379 A1 8/2013
CN 201134101 Y 10/2008
(Continued)

OTHER PUBLICATIONS

European Search Report and Written Opinion for the European Patent Application No. EP19194241, dated Oct. 22, 2019, 7 pages.
European Search Report for the European Patent Application No. EP03743667, dated Jul. 22, 2008.
International Search Report and Written Opinion dated Sep. 9, 2016, issued in PCT Patent Application No. PCT/US2016/037189, 14 pages.
(Continued)

*Primary Examiner* — Brandy S Lee
(74) *Attorney, Agent, or Firm* — Kacvinsky Daisak Bluni PLLC

(57) ABSTRACT

A drug delivery system having a drug delivery device and an associated sensor is provided. The sensor can be associated with a sensing site on user. The drug delivery device can be positioned over the sensor in any rotational position and can be associated with an infusion site on the user. The close positioning of the sensor and the drug delivery device allows data from the sensor to be relayed to the drug delivery device and then on to a remote control device. Further, the drug delivery device can be replaced at the end of its duration of use, which is shorter than the duration of use of the sensor, without disturbing the sensor. Subsequent drug delivery devices can then be used with the sensor while allowing each corresponding infusion site to be changed, thereby providing more efficient operation of the drug delivery system.

23 Claims, 11 Drawing Sheets

(51) Int. Cl.
*A61M 5/142* (2006.01)
*A61M 5/172* (2006.01)
*A61B 5/00* (2006.01)

(52) U.S. Cl.
CPC ......... *A61M 5/1723* (2013.01); *A61B 5/4839* (2013.01); *A61B 5/6849* (2013.01); *A61M 2005/1726* (2013.01); *A61M 2205/3303* (2013.01); *A61M 2205/3584* (2013.01); *A61M 2205/52* (2013.01)

(58) Field of Classification Search
CPC .. A61M 2005/1726; A61M 2205/3303; A61M 2205/3584; A61M 2205/52; A61M 5/14244; A61M 5/14248; A61M 5/16836; A61M 5/1723; A61M 5/46
See application file for complete search history.

(56) References Cited

U.S. PATENT DOCUMENTS

| | | | |
|---|---|---|---|
| 4,206,401 A | 6/1980 | Meyer | |
| 4,307,713 A | 12/1981 | Galkin et al. | |
| 4,398,542 A | 8/1983 | Cunningham et al. | |
| 4,560,979 A | 12/1985 | Rosskopf | |
| 4,587,850 A | 5/1986 | Moser | |
| 4,801,957 A | 1/1989 | Vandemoere | |
| 4,836,752 A | 6/1989 | Burkett | |
| 4,850,954 A | 7/1989 | Charvin | |
| 4,882,600 A | 11/1989 | Van de Moere | |
| 4,961,055 A | 10/1990 | Habib et al. | |
| 4,973,998 A | 11/1990 | Gates | |
| 5,045,871 A | 9/1991 | Reinholdson | |
| 5,239,326 A | 8/1993 | Takai | |
| 5,452,033 A | 9/1995 | Balling et al. | |
| 5,563,584 A | 10/1996 | Rader et al. | |
| 5,576,781 A | 11/1996 | Deleeuw | |
| 5,585,733 A | 12/1996 | Paglione | |
| 5,586,553 A | 12/1996 | Halili et al. | |
| 5,647,853 A | 7/1997 | Feldmann et al. | |
| 5,660,163 A | 8/1997 | Schulman et al. | |
| 5,726,404 A | 3/1998 | Brody | |
| 5,726,751 A | 3/1998 | Altendorf et al. | |
| 5,785,681 A | 7/1998 | Indravudh | |
| 5,800,420 A | 9/1998 | Gross et al. | |
| 5,830,999 A | 11/1998 | Dunn | |
| 5,867,688 A | 2/1999 | Simmon et al. | |
| 5,899,882 A | 5/1999 | Waksman et al. | |
| 6,171,264 B1 | 1/2001 | Bader | |
| 6,381,029 B1 | 4/2002 | Tipirneni | |
| 6,685,452 B2 | 2/2004 | Christiansen et al. | |
| 6,768,319 B2 | 7/2004 | Wang | |
| 6,830,558 B2 | 12/2004 | Flaherty et al. | |
| 7,018,360 B2 | 3/2006 | Flaherty et al. | |
| 7,128,727 B2 | 10/2006 | Flaherty et al. | |
| 7,144,384 B2 | 12/2006 | Gorman et al. | |
| 7,182,726 B2 | 2/2007 | Williams et al. | |
| 7,303,073 B2 | 12/2007 | Raynal-Olive et al. | |
| 8,056,719 B2 | 11/2011 | Porret et al. | |
| 8,105,282 B2 | 1/2012 | Susi et al. | |
| 8,285,487 B2 | 10/2012 | Bergstrom et al. | |
| 8,454,557 B1 | 6/2013 | Qi et al. | |
| 8,461,561 B2 | 6/2013 | Freeman et al. | |
| 8,727,117 B2 | 5/2014 | Maasarani | |
| 9,005,166 B2 | 4/2015 | Uber, III et al. | |
| 9,248,229 B2 | 2/2016 | Devouassoux et al. | |
| 9,427,710 B2 | 8/2016 | Jansen | |
| 9,598,195 B2 | 3/2017 | Deutschle et al. | |
| 9,862,519 B2 | 1/2018 | Deutschle et al. | |
| 10,086,131 B2 | 10/2018 | Okihara | |
| 10,342,926 B2 | 7/2019 | Nazzaro et al. | |
| 10,441,717 B2 | 10/2019 | Schmid et al. | |
| 10,894,122 B2* | 1/2021 | Nishimura | A61M 5/14248 |
| 2002/0032374 A1 | 3/2002 | Holker et al. | |
| 2002/0161307 A1 | 10/2002 | Yu et al. | |
| 2003/0073952 A1 | 4/2003 | Flaherty et al. | |
| 2004/0010207 A1 | 1/2004 | Flaherty et al. | |
| 2004/0010507 A1 | 1/2004 | Bellew | |
| 2004/0085215 A1 | 5/2004 | Moberg et al. | |
| 2004/0215492 A1 | 10/2004 | Choi | |
| 2005/0055242 A1 | 3/2005 | Bello et al. | |
| 2005/0238507 A1 | 10/2005 | Dilanni et al. | |
| 2006/0086909 A1 | 4/2006 | Schaber | |
| 2006/0092569 A1 | 5/2006 | Che et al. | |
| 2006/0282290 A1 | 12/2006 | Flaherty et al. | |
| 2007/0027370 A1 | 2/2007 | Brauker et al. | |
| 2007/0078784 A1 | 4/2007 | Donovan et al. | |
| 2007/0118405 A1 | 5/2007 | Campbell et al. | |
| 2007/0179885 A1 | 8/2007 | Bird et al. | |
| 2007/0191770 A1 | 8/2007 | Moberg et al. | |
| 2007/0233051 A1 | 10/2007 | Hohl et al. | |
| 2008/0004515 A1 | 1/2008 | Jennewine | |
| 2008/0027371 A1 | 1/2008 | Higuchi et al. | |
| 2008/0033272 A1 | 2/2008 | Gough et al. | |
| 2008/0077081 A1* | 3/2008 | Mounce | A61M 5/1413 604/67 |
| 2008/0173073 A1 | 7/2008 | Downie et al. | |
| 2008/0255438 A1 | 10/2008 | Saidara et al. | |
| 2008/0269723 A1 | 10/2008 | Mastrototaro et al. | |
| 2008/0281290 A1 | 11/2008 | Yodfat et al. | |
| 2009/0062767 A1 | 3/2009 | Van Antwerp et al. | |
| 2009/0069787 A1 | 3/2009 | Estes et al. | |
| 2009/0112769 A1 | 4/2009 | Dicks et al. | |
| 2009/0254041 A1 | 10/2009 | Krag et al. | |
| 2010/0076275 A1 | 3/2010 | Chu et al. | |
| 2010/0094251 A1 | 4/2010 | Estes | |
| 2010/0137784 A1 | 6/2010 | Cefai et al. | |
| 2010/0145272 A1 | 6/2010 | Cefai et al. | |
| 2010/0185175 A1 | 7/2010 | Kamen et al. | |
| 2010/0286997 A1 | 11/2010 | Srinivasan | |
| 2011/0124996 A1 | 5/2011 | Reinke et al. | |
| 2011/0142688 A1 | 6/2011 | Chappel et al. | |
| 2011/0152658 A1 | 6/2011 | Peyser et al. | |
| 2011/0213306 A1 | 9/2011 | Hanson et al. | |
| 2011/0218495 A1 | 9/2011 | Remde | |
| 2011/0225024 A1 | 9/2011 | Seyer et al. | |
| 2011/0246235 A1 | 10/2011 | Powell et al. | |
| 2011/0313680 A1 | 12/2011 | Doyle, III et al. | |
| 2011/0316562 A1 | 12/2011 | Cefai et al. | |
| 2012/0029941 A1 | 2/2012 | Malave et al. | |
| 2012/0050046 A1 | 3/2012 | Satorius | |
| 2012/0054841 A1 | 3/2012 | Schultz et al. | |
| 2012/0153936 A1 | 6/2012 | Romani et al. | |
| 2012/0182939 A1 | 7/2012 | Rajan et al. | |
| 2012/0184909 A1 | 7/2012 | Gyrn | |
| 2012/0203085 A1 | 8/2012 | Rebec | |
| 2012/0232520 A1 | 9/2012 | Sloan et al. | |
| 2012/0265166 A1 | 10/2012 | Yodrat | |
| 2012/0277667 A1* | 11/2012 | Yodat | A61M 5/1456 604/65 |
| 2013/0030841 A1 | 1/2013 | Bergstrom et al. | |
| 2013/0036100 A1 | 2/2013 | Nagpal et al. | |
| 2013/0060194 A1 | 3/2013 | Rotstein | |
| 2013/0080832 A1 | 3/2013 | Dean et al. | |
| 2013/0138452 A1 | 5/2013 | Cork et al. | |
| 2013/0173473 A1 | 7/2013 | Birtwhistle et al. | |
| 2013/0245545 A1 | 9/2013 | Arnold et al. | |
| 2013/0274576 A1* | 10/2013 | Amirouche | A61B 5/14503 600/365 |
| 2014/0114277 A1 | 4/2014 | Eggert et al. | |
| 2014/0163664 A1 | 6/2014 | Goldsmith | |
| 2014/0180203 A1 | 6/2014 | Budiman et al. | |
| 2015/0038898 A1 | 2/2015 | Palmer et al. | |
| 2015/0057913 A1 | 2/2015 | Benhammou | |
| 2015/0290391 A1 | 10/2015 | Schmid et al. | |
| 2016/0022905 A1 | 1/2016 | Nagar et al. | |
| 2016/0184517 A1 | 6/2016 | Baek et al. | |
| 2017/0173261 A1* | 6/2017 | O'Connor | A61M 5/1723 |

FOREIGN PATENT DOCUMENTS

| | | |
|---|---|---|
| EP | 1762263 A1 | 3/2007 |
| EP | 1839694 A1 | 10/2007 |
| EP | 1852703 A1 | 11/2007 |

(56) References Cited

FOREIGN PATENT DOCUMENTS

| | | |
|---|---|---|
| EP | 24453628 | 4/2008 |
| EP | 2099384 A1 | 9/2009 |
| EP | 2353628 A2 | 8/2011 |
| EP | 3068290 A1 | 9/2016 |
| ES | 2559866 T3 | 2/2016 |
| GB | 1401588 A | 7/1975 |
| GB | 2176595 A | 12/1986 |
| GB | 2443260 A | 4/2008 |
| GB | 2443261 A | 4/2008 |
| GB | 2461086 A | 12/2009 |
| GB | 2495014 A | 3/2013 |
| GB | 2524717 A | 10/2015 |
| GB | 2525149 A | 10/2015 |
| JP | 2001190659 A | 7/2001 |
| JP | 2003154190 A | 5/2003 |
| JP | 2007144141 A | 6/2007 |
| JP | 2007307359 A | 11/2007 |
| JP | 2008242502 A | 10/2008 |
| JP | 2012210441 A | 11/2012 |
| WO | 9801071 A1 | 1/1998 |
| WO | 9819145 A1 | 5/1998 |
| WO | 9824495 A1 | 6/1998 |
| WO | 9841267 A1 | 9/1998 |
| WO | 0010628 A2 | 3/2000 |
| WO | 0013580 A1 | 3/2000 |
| WO | 0019887 A1 | 4/2000 |
| WO | 0061215 A1 | 10/2000 |
| WO | 0078210 A1 | 12/2000 |
| WO | 2005031631 A2 | 4/2005 |
| WO | 2007112034 A2 | 10/2007 |
| WO | 2008024814 A2 | 2/2008 |
| WO | 2009023634 A2 | 2/2009 |
| WO | 2009032399 A1 | 3/2009 |
| WO | 2010025433 A1 | 3/2010 |
| WO | 2010078434 A2 | 7/2010 |
| WO | 2010146579 A1 | 12/2010 |
| WO | 2011133823 A1 | 10/2011 |
| WO | 2013149186 A1 | 10/2013 |
| WO | 2014136105 A1 | 9/2014 |
| WO | 2017089289 A1 | 6/2017 |
| WO | 2017205816 A1 | 11/2017 |

OTHER PUBLICATIONS

International Preliminary Report on Patentability dated Dec. 21, 2017, issued in PCT Patent Application No. PCT/US2016/037189.
U.K. Intellectual Property Office, GB Application No. GB 1401587.9, "Search Report under Section 17(5)" dated Aug. 11, 2015, 3 pages.
European Patent Office, "Notification of Transmittal of the ISR and the Written Opinion of the International Searching Authority, or the Declaration," in PCT Application No. PCT/GB2015/050247, dated May 8, 2015, 15 pages.
Extended Search Report mailed Nov. 24, 2017, issued in European Patent Application No. 15779465.2, 10 pages.
PCT International Search Report and Written Opinion dated Jul. 8, 2015, received in corresponding PCT application No. PCT/US15/26875, 13 pages.
U.K. Intellectual Property Office, GB Application No. GB 1401588.7, "Search Report under Section 17(5)" dated Aug. 17, 2015, 3 pages.
U.K. Intellectual Property Office, GB Application No. GB 1401589.5, "Search Report under Section 17" dated Jul. 27, 2015, 3 pages.
European Patent Office, "Notification of Transmittal of the ISR and the Written Opinion of the International Searching Authority, or the Declaration," in PCT Application No. PCT/GB2015/050250, dated May 7, 2015, 9 pages.
3GPP TS 23.003 V10.0.0.0 Numbering, addressing and identification. Dec. 2010.
European Patent Office, "Notification of Transmittal of the ISR and the Written Opinion of the International Searching Authority, or the Declaration," in PCT Application No. PCT/GB2015/050251, dated Jun. 12, 2015, 10 pa.
International Preliminary Report on Patentability for the International Patent Application No. PCT/US2017/061095, dated May 23, 2019, 2019, 7 pages.
International Search Report and Written Opinion for PCT/US18/52468, dated Feb. 26, 2019, 16 pages.
International Search Report and Written Opinion for PCT/US2017/061095, dated Feb. 20, 2018, 8 pages.
European Search Report for the European Patent Application No. EP19194241, dated Oct. 22, 2019, 7 pages.

\* cited by examiner

DRUG DELIVERY SYSTEM WITH SENSOR HAVING OPTIMIZED COMMUNICATION AND INFUSION SITE

TECHNICAL FIELD

Embodiments generally relate to medication delivery. More particularly, embodiments relate to drug delivery systems that rely on associated sensors.

BACKGROUND

Many conventional drug delivery systems include a drug delivery device and an associated sensor. The sensor can determine and store data related to a user of the drug delivery device. The drug delivery device can then be operated based on the data related to the user. Often, the sensor and the drug delivery device are controlled by a remote device. Conventional sensors generally operate at low power levels to conserve resources. As a result of low transmission power levels, many conventional sensors cannot always relay the stored data to the remote control to ensure efficient operation of the drug delivery device. Further, many conventional drug delivery systems that combine or collocate the sensor and the drug delivery device fail to account for the different durations of use of the sensor and the drug delivery device. As a result, either the sensor is prematurely replaced or the infusion site of the drug delivery device is not spaced far enough away or changed frequently enough in relation to the sensing site of the cannula.

Accordingly, there is a need for a drug delivery system that includes a drug delivery device and associated sensor that ensures data from the sensor can be provided to a remote controller device and improves management of the infusion site in view of the sensing site.

DETAILED DESCRIPTION

This disclosure presents various systems, components, and methods related to a drug delivery system. Each of the systems, components, and methods disclosed herein provides one or more advantages over conventional systems, components, and methods.

Various embodiments include a drug delivery system having a drug delivery device and an associated sensor. The sensor can be associated with a sensing site on the body of a user. The drug delivery device can be positioned over the sensor in any rotational position and can be associated with an infusion site on the body of the user. The close positioning of the sensor and the drug delivery device allows data from the sensor to be relayed to the drug delivery device and then on to a remote control device. Further, the drug delivery device can be replaced at the end of its duration of use, which is shorter than the duration of use of the sensor, without disturbing the sensor. One or more subsequent drug delivery devices can be used with the sensor while allowing each corresponding infusion site to be changed, thereby providing more efficient operation of the drug delivery system. Other embodiments are disclosed and described.

Figure 1:
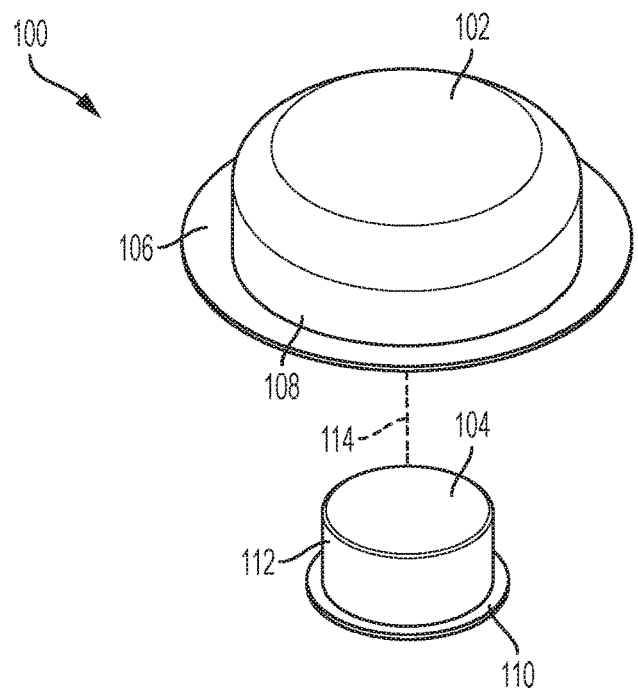
FIG. 1 illustrates an exemplary drug delivery system.

FIG. 1 illustrates an exemplary drug delivery system 100. The drug delivery system 100 can include a drug delivery device 102 and a sensor 104. The drug delivery device 102 can be any type of drug delivery device. The drug delivery device 102 can deliver any type of drug or therapeutic agent to a user. In various embodiments, the drug delivery device 102 can store and deliver insulin to a user and can be considered to be a drug delivery device "pump." FIG. 1 shows a first view of the drug delivery system 100.

The sensor 104 can be any type of sensor. The sensor 104 can monitor one or more health, biological, biomedical, or medical conditions of a user. In various embodiments, the sensor can be a continuous glucose monitoring (CGM) sensor.

As shown in FIG. 1, the drug delivery device 102 can include a base component 106 and a housing component 108. The base 106 can be considered a lip component or portion that extends around and beyond the housing 108. The housing 108 can be cylindrically shaped with a circular cross-sectional profile and a tapered top portion but is not so limited. The base 106 can also be circular but is not so limited. In various embodiments, the circular base 106 can have a diameter that is larger than a diameter of the housing 108 such that the base 106 includes an edge or lip portion that extends beyond the outer diameter of the housing 108. The drug delivery device 102 can include all components for storing a liquid drug or other therapeutic agent and providing the stored liquid drug or therapeutic agent to a user of one or more doses.

The CGM sensor 104 can include a base component 110 and a housing component 112. The base 110 can include a lip component or portion that extends around and beyond the housing 112. The housing 112 can be cylindrically shaped with a circular cross-sectional profile but is not so limited. The base 110 can also be circular but is not so limited. In various embodiments, the circular base 110 can have a diameter that is larger than a diameter of the housing 112 such that the base 110 includes an edge or lip portion that extends beyond the outer diameter of the housing 112. The CGM sensor 104 can include all components for monitoring glucose levels of a user. The drug delivery device 102 and the CGM sensor 104 can each have any size, shape, or form factor. In general, the drug delivery device 102 and the CGM sensor 104 can each be made to be small and compact with low profile form factors (e.g., as shown in FIG. 1) to maximize comfort for a user while remaining inconspicuous.

In various embodiments, the drug delivery system 100 can be a wearable drug delivery system. For example, the drug delivery system 100 can be worn directly on the body or skin of a user. In various embodiments, the CGM sensor 104 can be positioned within a central opening of the drug delivery device 102 (as indicated by indicator 114). In such embodiments, the base 110 and the housing 112 of the CGM sensor 104 can fit within the central cavity of the drug delivery device 102. The drug delivery device 102 can fit over the CGM sensor 104 such that the bottom surfaces of the drug delivery device 102 and the CGM sensor 104 are aligned and/or level (e.g., coplanar). In this way, the drug delivery system 100 can be easily attached to a user and can rest comfortably on the user.

In various embodiments, the arrangement of the drug delivery device 102 and the CGM sensor 104 allows the drug delivery device 102 to be removed and replaced. When replacing the drug delivery device 102, a new drug delivery device 102 can be positioned on top of the CGM sensor 104. The CGM sensor 104 can generally have a duration of use that is longer than the duration of use of the drug delivery device 102. In various embodiments, the CGM sensor 104 can have a first duration of use that can be approximately twelve (12) days. During the duration of use of the CGM sensor 104, a sensing cannula of the CGM sensor 104 can remain fixed in place (e.g., within the body of the user).

In various embodiments, the drug delivery device 102 can have a duration of use that can be approximately three (3) days. During the duration of use of the drug delivery device 102, an infusing cannula of the drug delivery device 102 can remain fixed in place (e.g., within the body of the user). With the drug delivery system 100, the infusion site for a user can be changed each time the drug delivery device 102 is replaced. This is advantageous as an infusion site can become less effective after roughly three (3) days of use.

Accordingly, when a first drug delivery device 102 is removed and replace with a second drug delivery device 102, the infusion site can be changed. The drug delivery device 102 can be replaced several times (e.g., four (4) times) before both the last drug delivery device 102 and the CGM sensor 104 are both removed and replaced together (e.g., at a new site on the body of the user). In this way, the drug delivery system 100 enables a sensing site for glucose monitoring to be maintained for the entire duration of use of the CGM sensor—which increases the effectiveness of the monitoring or sensing site—while providing the flexibility to adjust the infusion site.

Figure 2:
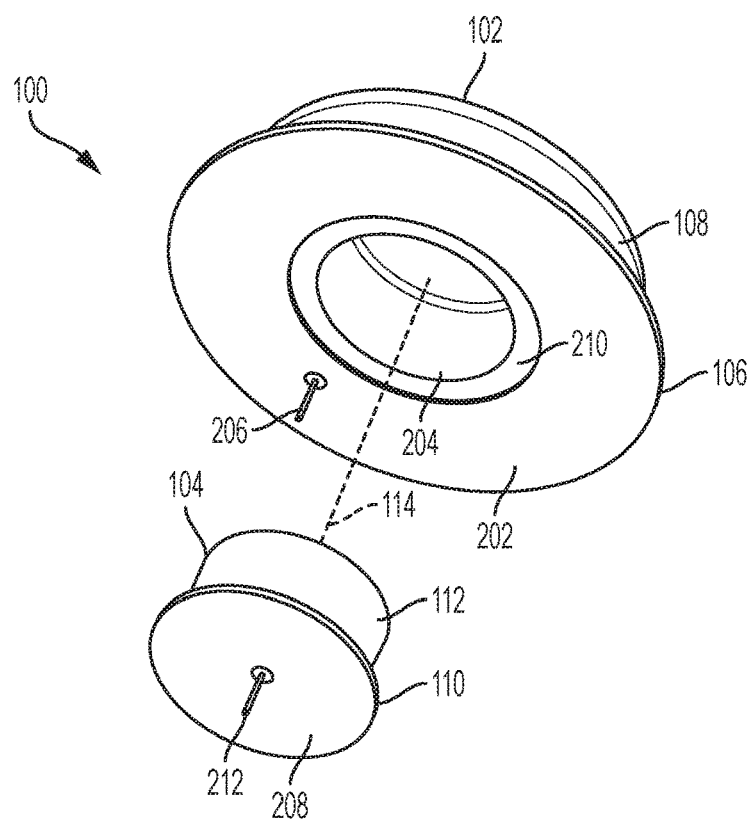
FIG. 2 illustrates a second view of the drug delivery system depicted in FIG. 1.

FIG. 2 illustrates a second view of the drug delivery system 100. An underside of the drug delivery system 100 is shown in FIG. 2. As shown, the drug delivery device 102 can include a bottom surface 202 and an opening or cavity 204. The opening 204 can be positioned in a center of the bottom surface 202. The opening 204 can be circular but is not so limited. In generally, the opening 204 can be shaped to accommodate the drug delivery device 102 fitting over the CGM sensor 104. The bottom surface 202 can also be circular with an inner diameter (e.g., defining a boundary of the outer portion of the opening and an inner portion of the bottom surface 202) and an outer diameter (e.g., defining a boundary of the outer portion of the bottom surface 202). A cannula 206 (e.g., an infusion cannula) can extend from the bottom surface 202. The cannula 206 can be positioned along any portion of the bottom surface 202 (e.g., offset from a center of the bottom surface 202).

As further shown in FIG. 2, the CGM sensor 104 can include a bottom surface 208. The bottom surface 208 can be circular but is not so limited. An outer portion of the base 110 can fit or be positioned within a recess 210 of the base 106 of the drug delivery device 102. The recess 210 can be positioned around the opening 204. When the CGM sensor 104 is positioned within the opening 204, the outer edge of the bottom surface 208 can reside with the recess 210, thereby allowing the bottom surface 202 and the bottom surface 208 to form a substantially flat surface (e.g., to be aligned or coplanar and/or to form a single continuous surface as felt by the user wearing the drug delivery system 100).

A cannula 212 (e.g., a sensing cannula) can extend from the bottom surface 208. The cannula 212 can be positioned along any portion of the bottom surface 208. In various embodiments, the cannula 212 can extend from a center of the bottom surface 208.

Figure 3:
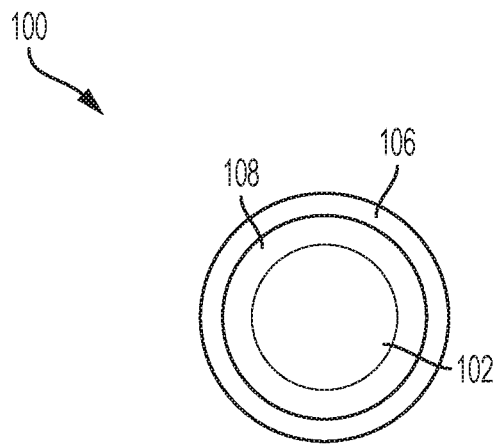
FIG. 3 illustrates an overhead view of the drug delivery system depicted in FIG. 1.

FIG. 3 illustrates an overhead view of the drug delivery system 100. As shown, the drug delivery device 102 covers the CGM sensor 104 such that the CGM sensor 104 is not visible from an overhead view of the drug delivery system 100. An outer portion of the base 106 extends beyond the housing 108. Accordingly, in various embodiments, the width, diameter, and/or perimeter of the base 106 may be larger than the width, diameter, and/or perimeter of the housing 108.

Figure 4:
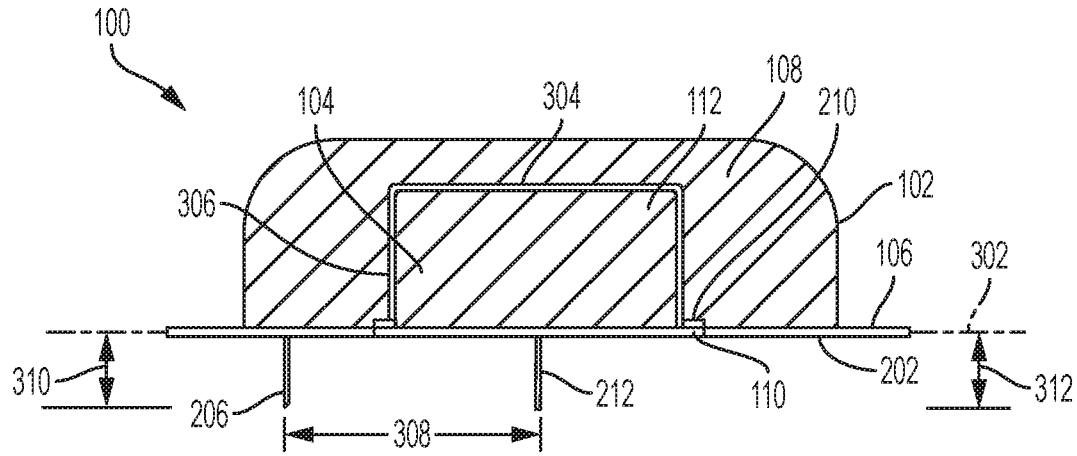
FIG. 4 illustrates a cross-sectional side view of the drug delivery system depicted in FIG. 1.

FIG. 4 illustrates a cross-sectional side view of the drug delivery system 100. As shown, the CGM sensor 104 is positioned within the opening 204 of the drug delivery device 102. The CGM 104 can be positioned within the opening 204 such that the bottom surface 208 of the CGM sensor 104 is aligned with the bottom surface 202 of the drug delivery device 102. In various embodiments, the bottom surfaces 202 and 208 can be substantially coplanar—e.g., aligned along an axis 302 as shown in FIG. 4. As shown, in various embodiments, the drug delivery device 102 can cover all outer surfaces of the CGM sensor 104 other than the bottom surface 208 of the CGM sensor 104—such that, for example, the CGM sensor 104 is encapsulated by the drug delivery device 102 and the body of the user.

FIG. 4 shows a first clearance or distance (or space or spacing) 304 between a top of the housing 112 and an inner upper surface of the housing 108. FIG. 4 shows a second clearance or distance (or space or spacing) 306 between an outer diameter of the housing 112 and a diameter of the opening 204. The first and second clearances 304 and 306 can be of any size. In general, the first and second clearances 304 and 306 can be relatively small (e.g., relative to the overall width of the drug delivery system 100) such that the CGM sensor 104 forms a tight fit inside the opening 204.

As further shown in FIG. 4, an outer portion or lip of the base 110 is positioned within the recess 210 to facilitate the alignment of the bottom surfaces 202 and 208. The cannula 214 is shown spaced a distance 308 from the cannula 206. The distance 308 can be a minimum distance. As the drug delivery device 102 (or a replacement drug delivery device 102) can be positioned over the CGM sensor 104 in any rotational position relative to the CGM sensor 104, the cannula 206 can be positioned the distance 308 away from the cannula 212 according to any rotational position (e.g., along any position along a circle having a radius of distance 308; 360 degrees around the site of the cannula 212).

The cannula 206 can have a depth (e.g., an infusion depth) 310. Similarly, the cannula 212 can have a depth (e.g., a sensing depth) 312. The depths 310 and 312 can be the same depths (as shown in FIG. 4) but are not so limited. The position of the cannula 212 with respect to the body of a user can be considered to be a sensing site. The position of the cannula 206 with respect to the body of the user can be considered to be an infusion site.

In various embodiments, the drug delivery device 102 can be positioned over the CGM sensor 104 in any orientation—for example, the infusion site can be spaced the distance 308 from the sensing site at any angular orientation relative to the sensing site. This allows the infusion site provided by the cannula 206 to be rotated or adjusted around the body of the user while the sensing site remains fixed—for example, when the drug delivery device 102 is removed and replaced with a subsequent or next drug delivery device 102. When removing the drug delivery device 102, the attachment of the CGM sensor 104 can be undisturbed. The next drug delivery device 102 can then be placed over and fitted on top of the CGM sensor 104 in the same manner the original drug delivery device 102 was placed over the CGM sensor 104. Again, this allows the CGM sensor to operate using a sensing site that remains fixed over the duration of use of the CGM sensor while the infusion sites associated with one or more corresponding drug delivery devices 102 can be changed with each new drug delivery device 102.

Figure 5:
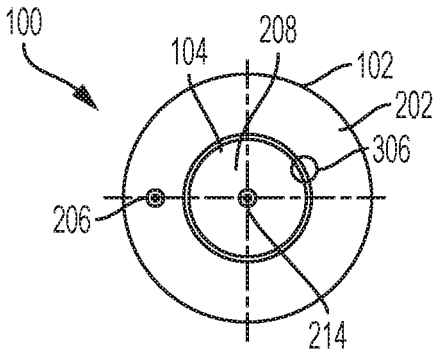
FIG. 5 illustrates an underside view of the drug delivery system depicted in FIG. 1.

FIG. 5 illustrates an underside view of the drug delivery system 100 (e.g., a view of the bottom of the drug delivery system 100). As shown, the CGM sensor 104 is positioned within the opening 204 with the clearance 306 separating the CGM sensor 104 from the drug delivery device 102. The cannula 206 is shown separated by the distance 308 from the cannula 212. The bottom surface 202 and/or the bottom surface 208 can include an adhesive to facilitate coupling to the body (e.g., skin) of a user. Any portion of the bottom surface 202 can include an adhesive. Similarly, any portion of the bottom surface 208 can include an adhesive. The adhesive on the bottom surface 208 can be the same adhesive on the bottom surface 202 or can be a different adhesive.

Figure 6:
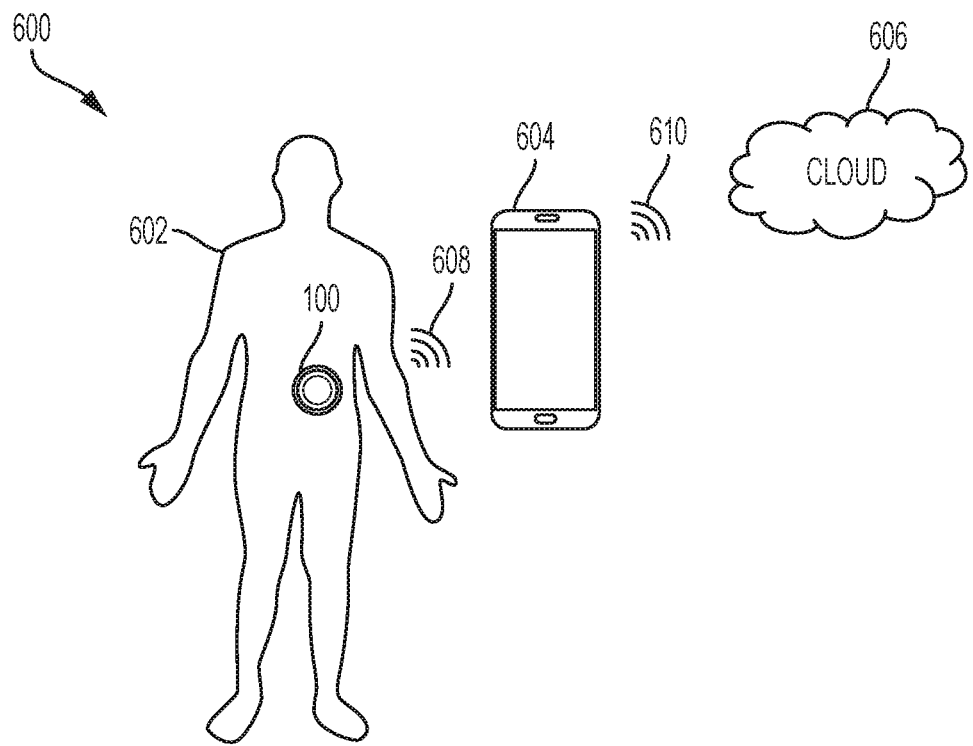
FIG. 6 illustrates an exemplary operating environment of the drug delivery system depicted in FIG. 1.

FIG. 6 illustrates an exemplary operating environment 600 of the drug delivery system 100. As shown in FIG. 6, the operating environment can include a user or patient 602, the drug delivery system 100, a controller device 604, and a remote or cloud computing component 606. The user 602 can be a user of the drug delivery system 100. The controller device 604 can be a handheld computing device including a dedicated (e.g., customized) controller or a smartphone for controlling operation of the drug delivery system 100. In various embodiments, the controller device 604 can be a tablet or a desktop computer. In general, the controller device 604 can be any computing device, including a mobile computing device, and can be a commercial off the shelf (COTS) computing device or a customized computing device. The controller device 604 can be used by the user 602 to manage operation of the drug delivery system 100 and to visually observe performance information related to operation of the drug delivery system 100.

The cloud component 606 can represent a remote computing platform. The cloud component 606 can monitor operation of the drug delivery system 100 through connectivity with the controller device 604. The cloud component 606 can store and analyze data related to operation of the drug delivery system 100 (e.g., as determined or adjusted by the controller device 604). The cloud component 606 can be connected to one or more remote computing devices to facilitate viewing or manipulation of any stored operational data. For example, a mobile device of a remote caregiver can receive operational data stored by the cloud component 606 for viewing and/or manipulation.

In various embodiments, a communications link 608 can provide connectivity between the drug delivery system 100 and the controller device 604 and a communications link 610 can provide connectivity between the controller device 604 and the cloud component 606. The communication links 608 and 610 can be bi-direction communication links and can include wired, wireless, optical, and/or infrared communication links. The communication links 608 and 610 can operate according to any known communications standard or protocol over any type of communications medium or link. In various embodiments, a computing device coupled to the cloud component 606 can control operation of the drug delivery system 100 (e.g., by a caregiver during an emergency).

In various embodiments, the CGM sensor 104 can monitor glucose levels and store data indicative of the same. This data can be provided to the drug delivery device 102 to adjust operation of the drug delivery device 102. In various embodiments, data from the CGM sensor 104 can be passed along to the controller device 604 and/or the cloud component 606 by the drug delivery device 102.

To facilitate data sharing between the CGM sensor 104 and the drug delivery device 102, the CGM sensor and the drug delivery device 102 can be connected over a wired, wireless, optical, and or infrared communication link. The communication link coupling the CGM sensor 104 to the drug delivery device 102 can operate according to any known communications standard or protocol over any type of communications medium or link.

In various embodiments, the drug delivery device 102 can communicate with the controller device 604 over Bluetooth Low Energy (BLE). In various embodiments, the CGM sensor 104 can communicate with the drug delivery device 102 over Near-field communication (NFC), a radio-frequency (RF) communication standard, or BLE. In general, the drug delivery device 102 can include more resources (e.g., power resources and/or transmission signal strength) for providing more reliable communications with the controller device 604 compared to the resources (e.g., power resources and/or transmission signal strength) of the CGM sensor 104 for communicating with the drug delivery device 102.

For conventional CGM sensors that communicate with separate (e.g., de-coupled) conventional drug delivery devices, the conventional CGM sensors often are unable to relay stored data to a conventional controller device—e.g., because the communication protocol and/or transmission levels of the conventional CGM sensors are often too low such that the conventional controller devices are often out of range of the conventional CGM sensors. As a result, many conventional CGM sensors cannot provide their monitored glucose data to a conventional controller device such that the data can be used to more efficiently operate a conventional drug delivery device. As a result, often the data collected by the conventional CGM sensor is lost or unused. Alternatively, a user of such a conventional CGM sensor must awkwardly wave her conventional controller device over the conventional CGM sensor repeatedly to ensure reception of the transmitted data. "Picking up" the stored glucose data from the conventional CGM sensor in this manner is often required during inconvenient times for the user, making the process cumbersome and undesirable.

In contrast to such conventional systems and conventional CGM sensors, the drug delivery system 100 provides improved communication capabilities by closely locating (e.g., co-locating) the CGM sensor 104 with the drug delivery device 102. In doing so, even if the CGM sensor 104 uses a traditionally low power method of communication (e.g., a low power wireless standard), the drug delivery device 102 can detect any data transmission from the CGM sensor 104 due to the close proximity of the CGM sensor 104 and the drug delivery device 102. As a result, data from the CGM sensor 104 can be relayed to the controller device 604 (and subsequently on to the cloud component 606) by the drug delivery device 102. In turn, the drug delivery device 102 can be operated more efficiently to better manage the health of the user 602.

Figure 7:
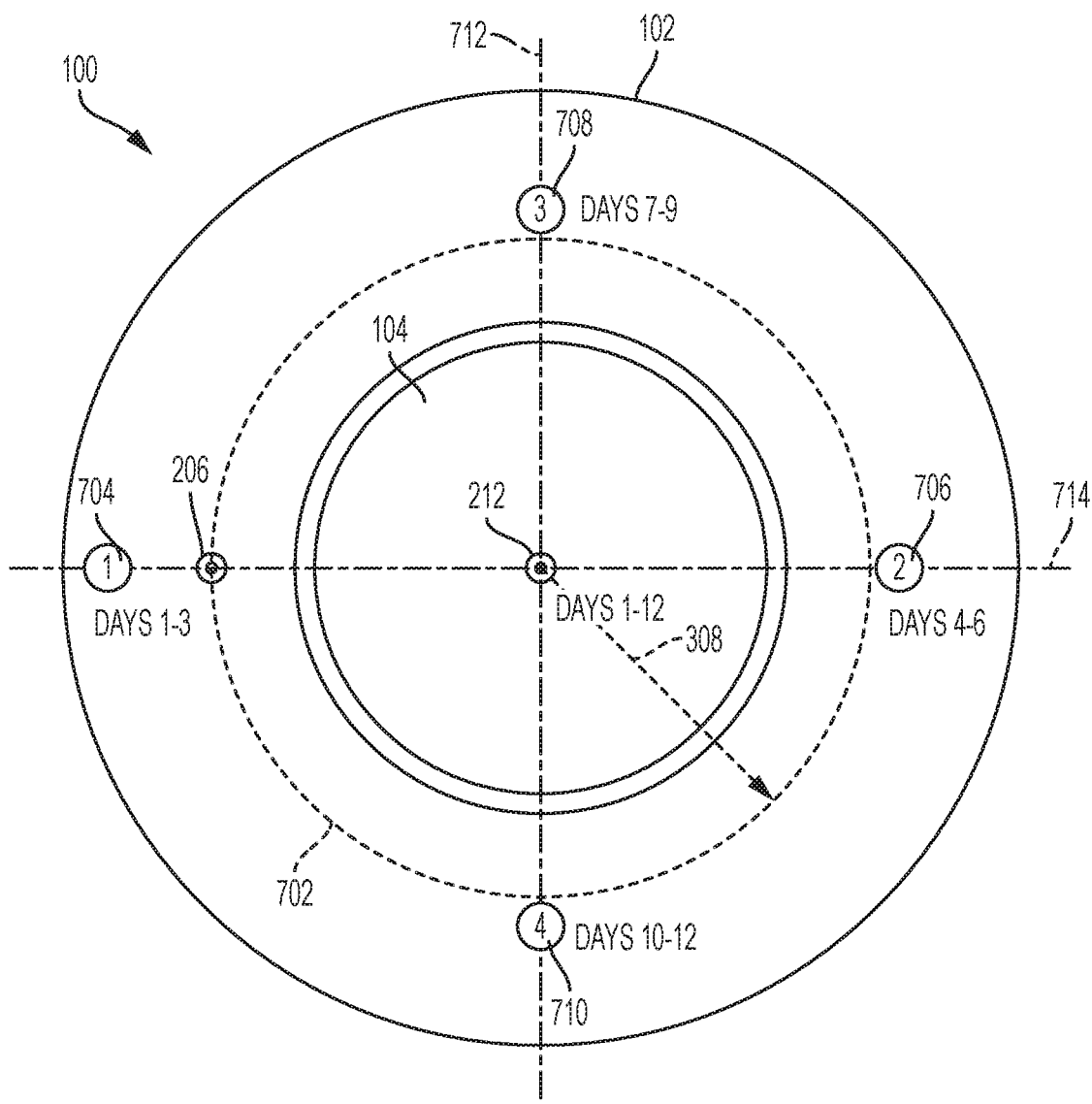
FIG. 7 illustrates an exemplary rotation of infusion sites for a fixed position of a sensing site for the drug delivery system depicted in FIG. 1.

FIG. 7 illustrates an exemplary rotation of infusion sites for a fixed position of a sensing site for the drug delivery system 100 using, for example, multiple replacement drug delivery devices 102. FIG. 7 shows an underside or bottom view of the drug delivery system 100. As shown, an infusion site availability circle 702 surrounds the cannula 212 (or the site of the cannula 212 or sensing site). The circle 702 can be centered about the cannula 212 and can have a radius equal to the distance 308. The circle 702 can represent possible locations of the cannula 206 (or the site of the cannula 206 of the infusion site). Specifically, the cannula 206 can be positioned anywhere along the circle 702. As shown, the cannula 206 is shown positioned along the circle 702.

In various embodiments, the CGM sensor 104 can be worn by a patient for twelve (12) days. Accordingly, the cannula 212 is positioned as shown for the entirety of the twelve (12) days (e.g., the cannula 212 can be located as shown for the entire duration of use of the CGM sensor 104). In various embodiments, the drug delivery device 102 can be used for three (3) days and then replaced with another drug delivery device 102. In various embodiments, the position of the cannula 206 can be changed or adjusted for each new drug delivery device 102. In particular, the position of the cannula 206 can be rotated along the circle 702.

FIG. 7 shows an exemplary rotation of the infusion site provided by rotating the cannula 206 associated with each drug delivery device 102 used with the CGM sensor 104. As shown, site 704 can represent a first or initial site for cannula 206 (e.g., for days 1-3). The first site 704 can be positioned along a first central axis 714. The cannula 212 and the first site 704 can both be positioned along the central axis 714 separated by the distance 308.

Site 706 can represent a second site for the cannula 206 (e.g., for days 4-6). The second site 706 can represent the position of the cannula 206 when a second drug delivery device 102 replaces the first drug delivery device 102 that is associated with the first site 704. The second site 706 can also be positioned along the axis 714. The second site 706 can be positioned 180 degrees away from the first site 704 along the circle 702 relative to the fixed location of the cannula 212.

Site 708 can represent a third site for the cannula 206 (e.g., for days 7-9). The third site 708 can represent the position of the cannula 206 when a third drug delivery device 102 replaces the second drug delivery device 102 that is associated with the second site 706. The third site 708 can be positioned along a second central axis 712. The second central axis 712 can be perpendicular to the first central axis 714. The third site 708 can be positioned 90 degrees away from the second site 706 along the circle 702 relative to the fixed location of the cannula 212.

Site 710 can represent a fourth site for the cannula 206 (e.g., for days 10-12). The fourth site 710 can represent the position of the cannula 206 when a fourth drug delivery device 102 replaces the third drug delivery device 102 that is associated with the third site 708. The fourth site 710 can be positioned along the first axis 714. The fourth site 710 can be positioned 180 degrees away from the third site 708 along the circle 702 relative to the fixed location of the cannula 212.

FIG. 7 shows an exemplary rotation of the infusion site using the cannula 206. In general, any rotation of the cannula 206 along the circle 702 can be used with the position of the infusion site changing with each new drug delivery device 102. After the duration of use of the CGM sensor 104 has expired, a new sensing site for the cannula 212 can be chosen on the user. Further, infusion sites relative to the new sensing site (e.g., spaced a distance 308 away) can then also be chosen relative to the sensing site.

As described herein, a sensor and drug delivery device can have different durations of use. For example, a sensor (e.g., a CGM sensor) can be used for longer periods of time (e.g., coupled to a user) than a drug delivery device (e.g., a wearable drug delivery device such as an insulin pump). In various embodiments, a CGM may have a duration of use of 12 days or longer while a wearable drug delivery device may have a duration of use of 3 days. Accordingly, a drug delivery system incorporating a CGM sensor and a wearable drug delivery device that relies on the CGM sensor for effective operation is to account for the different durations of use in accordance with the techniques disclosed herein.

Further, a sensor (e.g., a CGM sensor) can be sterilized in a first manner that may not be compatible with a wearable drug delivery device. For example, a CGM sensor may be effectively sterilized using gamma radiation. However, for a wearable drug delivery device, which may include electronics, sterilization by gamma radiation may not be possible. Instead, for the wearable drug delivery device, Ethylene Oxide (EO) sterilization may be used, which is not compatible with the CGM sensor. Accordingly, a drug delivery system incorporating a CGM sensor and a wearable drug delivery device that relies on the CGM sensor for effective operation is to account for the different sterilization methods for the two components.

Lastly, many sensors such as a CGM sensor may need to be coupled to a use for a period of time before the site properly provides proper sensor measurements. That is, a CGM sensor may need to be in place for roughly a day or so before measurements made by the CGM sensor can be considered accurate and trustworthy. In contrast, the infusion site associated with a wearable drug delivery device may only be useable for a few days (e.g., at most 3 days) before the site becomes unusable (e.g., due to the user's body resisting the infusion site after a few days). Accordingly, a drug delivery system incorporating a CGM sensor and a wearable drug delivery device that relies on the CGM sensor for effective operation is to account for these different use restrictions.

The disclosed systems, devices, methods, and techniques disclosed herein can account for and accommodate these competing characteristics of a CGM sensor and wearable drug delivery device.

Figure 8:
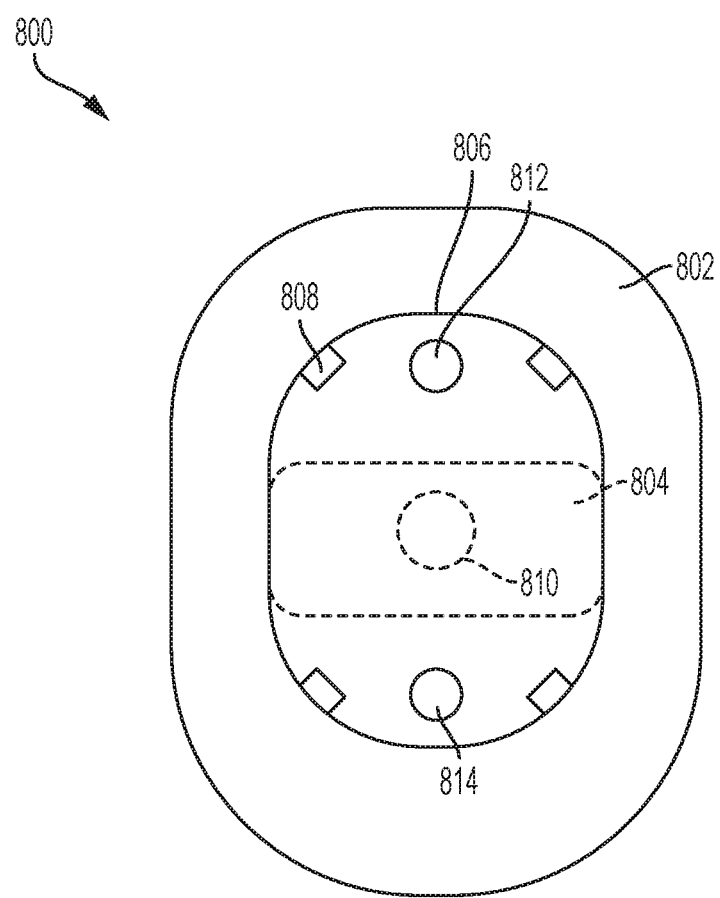
FIG. 8 illustrates an overhead view of a second exemplary drug delivery system.

FIG. 8 illustrates an overhead view of a portion of a second exemplary drug delivery system 800. The drug delivery system 800 can be alternative implementation of the drug delivery system 100. FIG. 8 shows an adhesive pad 802 and an incorporated sensor 804 (e.g., a CGM sensor). The CGM sensor 804 can be directly coupled to the adhesive pad 802. This arrangement allows the CGM sensor 804 and adhesive pad to be sterilized according to a first sterilization technique, such as gamma radiation. The cGM sensor 804 can be shown in phantom to show a possible position of the CGM sensor 804 and to reflect that it can be positioned on top of the adhesive pad 802 or can be positioned within an interior of the adhesive pad 802.

An outline 806 indicates where a drug delivery device (e.g., an insulin pump) can be attached to the adhesive pad 802 as described further herein. In various embodiments, the drug delivery device can be separately attached to the adhesive pad 802 having the incorporated CGM sensor 804. In this way, the drug delivery device can be sterilized according to a separate technique more suitable to the drug delivery device and then later coupled to the CGM sensor 804. The drug delivery device can be attached to the adhesive pad by a variety of techniques including using snaps or connectors 808. Any number of snaps and/or connectors 808 can be used.

Indicator 810 shows a position of a sensing site associated with the CGM sensor 804. That is, a sensing needle (or needles) can extend from the underside of the CGM sensor 804 at the site 810. The site 810 is shown in phantom to indicate that the site is position on the underside of the CGM sensor 804 at an opening of the adhesive pad 802. In various embodiments, the adhesive pad 802 can be positioned over an entirety of the underside of the CGM sensor 804 other than at the opening to accommodate the site 810.

In various embodiments, the adhesive pad 802 and the incorporated CGM sensor 804 can be attached to a user. The adhesive pad 802 and the incorporated CGM sensor 804 can be coupled to a user for a first period of time before a drug delivery device is coupled to the adhesive pad 802 and the incorporated CGM sensor 804 (or before a coupled drug delivery device is activated). In this way, the sensing site (or sites) associated with the adhesive pad 802 and the incorporated CGM sensor 804 can operate over the first period of time to reach a steady state (e.g., allowing the sensing sites to become reliable).

In various embodiments, once the CGM sensor 804 has been coupled to the user for a desired period do time, the drug delivery device can be coupled over the CGM sensor 804 and can be coupled to the adhesive pad 802 by the connectors 808. In various embodiments, the connectors 808 can be mechanical and can be, for example, latches or other devices providing a press fit.

In various embodiments, the adhesive pad 802 can include a first infusion site or opening 812 and a second infusion site or opening 814. The drug delivery device when attached to the adhesive pad 802 can use either the first or second openings 812 and 814 for deploying an infusion needle or cannula. As the adhesive pad 802 and the CGM sensor 804 can be coupled to the user for a period of time longer than the drug delivery device, an initial drug delivery device can be removed and replaced with a second drug delivery device. The first drug delivery device can use the first opening 812 for the infusion site. The second drug delivery device can use the second opening 814 for the infusion site. In this way, the infusion site can be rotated and changed over the duration of use of the adhesive pad 802 with the incorporated CGM sensor 804.

The openings 812 and 814 can be holes or openings within the adhesive pad 802. The adhesive pad 802 is no limited to the shape depicted. In various embodiments, the adhesive pad 802 can have any shape including round or oval. In various embodiments, the adhesive pad 802 can have multiple openings to facilitate rotation of the infusion site (e.g., more than the two openings 812 and 814). In various embodiments, the drug delivery device can be rotated in any manner with respect to the sensing site opening 810.

In various embodiments, the drug delivery system 800 can be used to initially attach the adhesive pad 802 with the incorporated CGM sensor 804 to a user. The CGM sensor 804 can be configured for operation and can be operated to have one or more sensing sites. After a period of time has elapsed, during which operation of the CGM sensor 804 reaches a steady state (e.g., at a time when measurements made by the CGM sensor 04 are accurate and/or reliable), the drug delivery device can be attached to the adhesive pad 802 (and positioned over top of the CGM sensor 804). The drug delivery device can use on of the two openings 812 and 814 for the first infusion site. After the drug delivery device has been used for a few days, it can be removed/de-coupled from the adhesive pad 802 and replaced with another drug delivery device. The second drug delivery device can use one of the openings 812 and 814 not used by the first drug delivery device. This process can be repeated until the duration of use of the CGM sensor 804 has been reached with each drug delivery device using a different infusion site from the prior drug delivery device.

Figure 9:
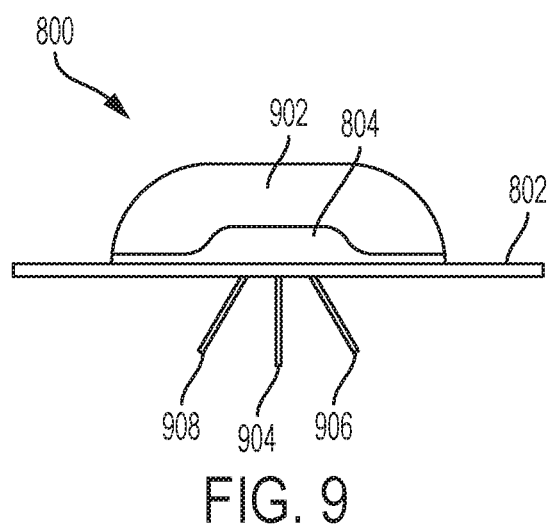
FIG. 9 illustrates a front view of the drug delivery system depicted in FIG. 8.

FIG. 9 illustrates a front view of the drug delivery system 800. As shown, the drug delivery system 800 shows the adhesive pad 802 having the incorporated CGM sensor 804 positioned over the adhesive pad 802. Further, a drug delivery device 902 is positioned over the CGM sensor 804. A first cannula 904 is positioned through one of the openings 812 and 814 to provide an infusion site. The first cannula 904 can be coupled to the drug delivery device 902. A second cannula 906 and a third cannula 908 can be coupled to the CGM sensor 804 and can provide first and second sensing sites, respectively. In various embodiments, a single sensing site can be provided and/or more than two sensing sites and cannulas can be used. As shown, the sensing sites provided by the cannulas 906 and 908 are spaced apart from the infusion site provided by the cannula 904.

The drug delivery system 800 and any constituent component thereof can have any size shape, and/or form factor and is not limited to the exemplary shapes shown in FIG. 9 (and/or FIGS. 8 and 10-13).

Figure 10:
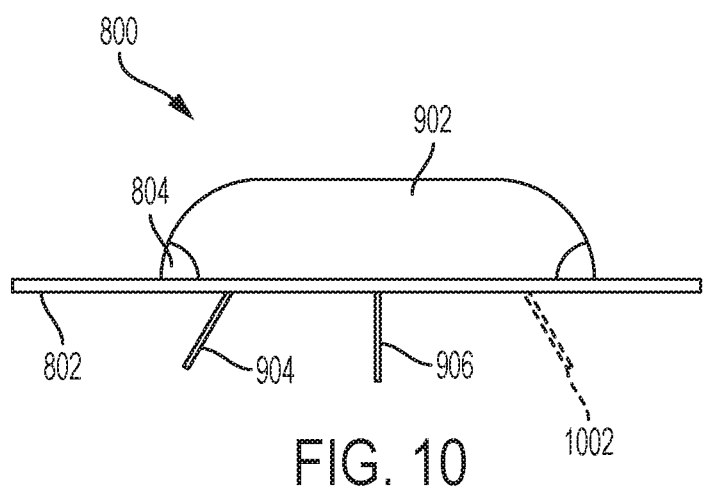
FIG. 10 illustrates a side view of the drug delivery system depicted in FIG. 8.

FIG. 10 illustrates a side view of the drug delivery system 800. As shown, the drug delivery device 902 is positioned over the CGM sensor 804 that is incorporated with the adhesive pad 802. The cannula 906 is shown positioned in an approximate middle of the drug delivery system 800. The cannula 904 is shown positioned at a first end of the drug delivery system 800—for example, using the opening 812. A second cannula 1002 is shown in phantom to represent the location of a second infusion site that can be used through opening 814 when the drug delivery device 902 is replaced.

Figure 11:
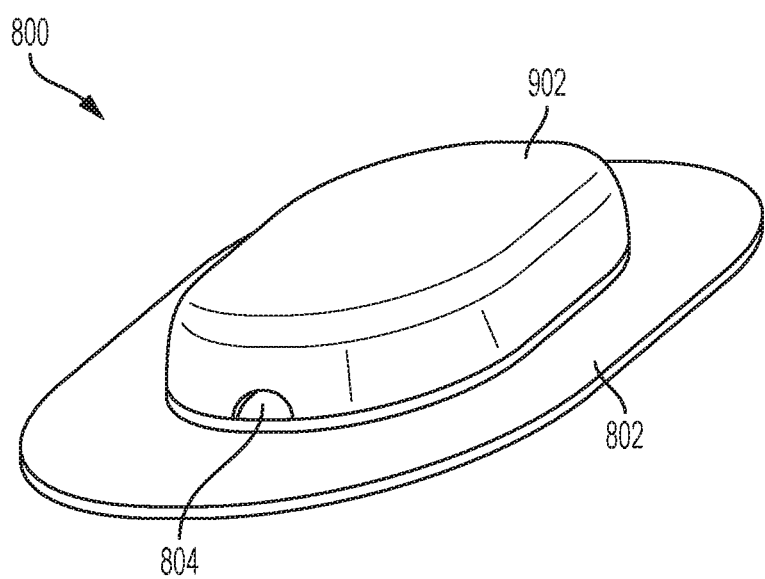
FIG. 11 illustrates an isometric view of the drug delivery system depicted in FIG. 8.

FIG. 11 illustrates an isometric view of the drug delivery system 800. As shown, the drug delivery device 802 is positioned over the CGM sensor 804 incorporated into the adhesive pad 802.

Figure 12:
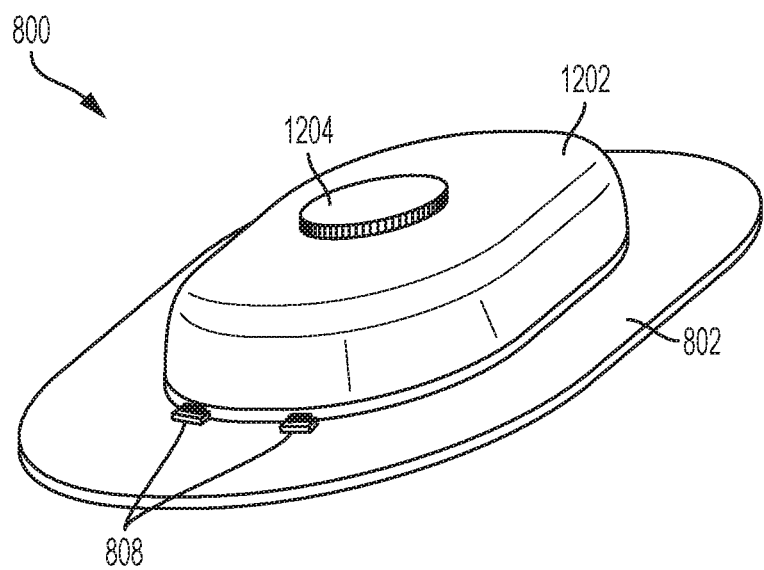
FIG. 12 illustrates a sensor configuration module of the drug delivery system depicted in FIG. 8.

FIG. 12 illustrates a CGM sensor configuration component or module 1202. The CGM sensor configuration module 1202 can be initially coupled to the CGM sensor 804 when provided to the user or can be later attached to the CGM sensor 804 by the user (e.g., using the connectors 808). The CGM sensor configuration module 1202 can be an entirely mechanical based system such that it can be sterilized in the same manner as the adhesive pad 802 and the CGM sensor 804. Alternatively, the CGM sensor configuration module 1202 can include electrical and/or electronical components such that it can undergo a different sterilization technique from the adhesive pad 802 and the CGM sensor 804. Under such a scenario, the CGM sensor configuration module 1202 can be coupled to the adhesive pad 802 and the CGM sensor 804 at a later time.

The CGM sensor configuration module 1202 can be used to configure operation of the CGM sensor 804. After configuring the CGM sensor 804, the CGM sensor configuration module 1202 can be removed and/or detached from the adhesive pad 802 and/or the CGM sensor 804 and replaced with the drug delivery device 902.

In various embodiments, the CGM sensor configuration module 1202 can include a user interface component 1204. The user interface component 1204 can comprise a button and/or a knob. In various embodiments, the user interface component 1204 can be used to activate the CGM sensor 804—for example, by the user turning a knob and/or pressing a button. In various embodiments, the user interface component 1204 can be used to set a number of sensing sites to be used (e.g., a number of sensing cannulas to deploy), set a depth of sensing (e.g., set a depth for each sensing cannula), and/or to trigger release of the cannulas. Once the one or more sensing cannulas (e.g., cannulas 906 and 908) are deployed, the CGM sensor 804 can begin operation.

After the CGM sensor configuration module 1202 has been used to configure operation of the CGM sensor 804, the CGM sensor configuration module 1202 can be removed from the adhesive pad 802. After the CGM sensor 804 has been operating for an appropriate amount of time, the drug delivery device 902 can be coupled to the adhesive pad 802 and positioned over the CGM sensor 804. The drug delivery device 902 can be coupled in a manner to enable glucose measurements or other data collected or derived by the CGM sensor 804 to be passed to the drug delivery device 902 for use in controlling operation of the drug delivery device 902 (e.g., adjusting a dose of a medicine provided to the user).

Figure 13:
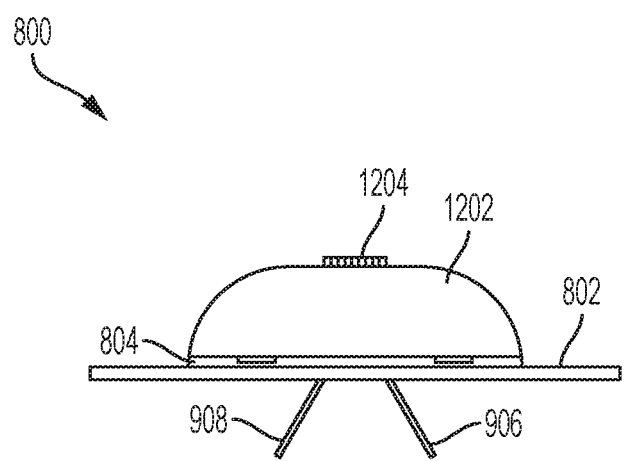
FIG. 13 illustrates a side view of the sensor configuration module depicted in FIG. 12.

FIG. 13 illustrates a side view of the CGM sensor configuration module 1202 depicted in FIG. 12. As shown in FIG. 13, the CGM sensor configuration module 1202 is positioned over the CGM sensor 804. The cannulas 906 and 908 have been deployed indicating the CGM sensor 804 has been configured for operation. Accordingly, the CGM sensor configuration module 1202 can be removed and replaced with the drug delivery device 902.

In various embodiments, the adhesive pad 802 can have any number of holes positioned on any portion of the adhesive pad 802. In various embodiments, the adhesive pad 802 can have four holes positioned a same distance from a center of a bottom surface of the adhesive pad 802. The four holes can be positioned along a circle that surrounds the center of the bottom surface of the adhesive pad 802, with the center representing a position from which the one or more sensing cannulas of the CGM sensor 804 extend.

In various embodiments, the CGM sensor 804 can be incorporated into the adhesive pad 802 to form a single combined component. In various embodiments, the CGM sensor 804 can only include mechanical components and does not contain any electrical components. In various embodiments, the drug delivery device 902 can include mechanical and/or electrical components. In various embodiments, the CGM sensor configuration module 1202 can include mechanical and/or electrical components. This can allow the drug delivery device 902 and the CGM sensor configuration module 1202 to undergo a sterilization process that is different from a sterilization process that the adhesive pad 802 and incorporated CGM sensor 804 can undergo. In various embodiments, the CGM sensor configuration module 1202 can include only mechanical components, allow the CGM sensor configuration module 1202, the adhesive pad 802, and the incorporated CGM sensor 804 to all undergo the same sterilization process and to be provided to a user connected together as one assembly. Then, once the user configures operation of the CGM sensor 104, the user can snap off the CGM sensor configuration module 1202 and replace it with the drug delivery device 902.

Figure 14:
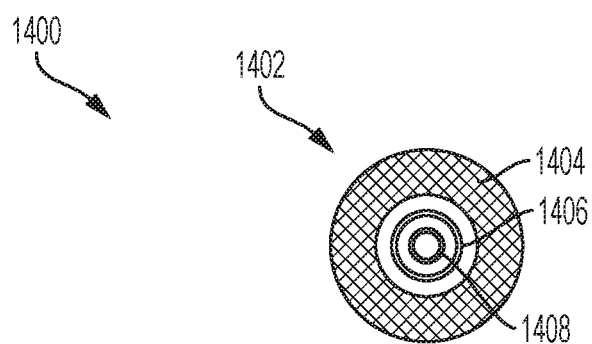
FIG. 14 illustrates a third exemplary drug delivery system.
Figure 14:
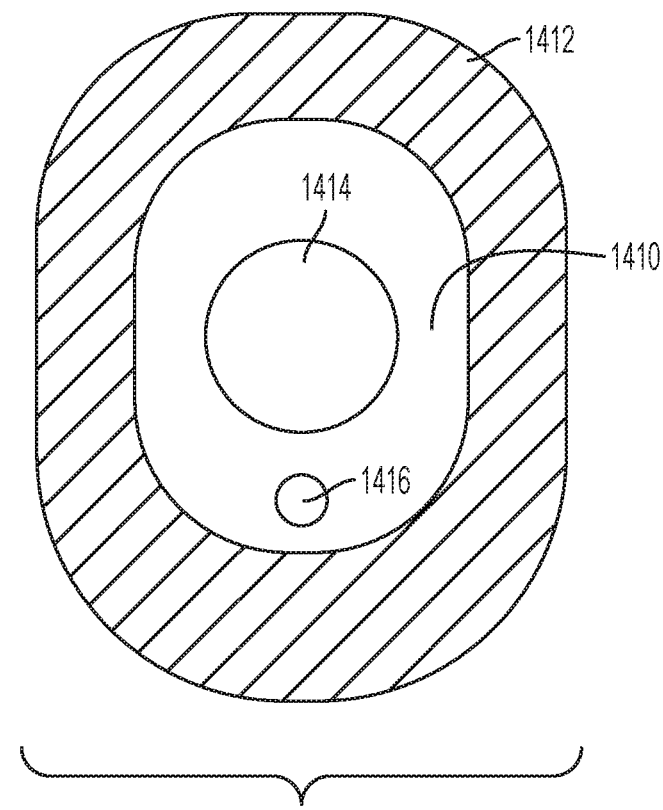

FIG. 14 illustrates a third exemplary drug delivery system 1400. The drug delivery system 1400 can be alternative implementation of the drug delivery system 100. As shown in FIG. 14, the drug delivery system 1400 can include a sensor 1402. The sensor 1402 can be a CGM sensor. FIG. 14 shows a view of the bottom or underside of the sensor 1402. In various embodiments, the CGM sensor 1402 can include an adhesive pad 1404, a first electrode 1406, and a second electrode 1408. The CGM sensor 1402 can be circularly-shaped but is not so limited.

In various embodiments, the adhesive pad 1404 can be positioned toward a periphery or outer portion of the bottom surface of the CGM sensor 1402. The adhesive pad 1404 can be arranged in a first circle. The first electrode 1406 can be positioned toward a middle portion of the bottom surface of the CGM sensor 1402. The first electrode 1406 can be arranged in a second circle (e.g., concentric with the first circle of the adhesive pad 1404 and smaller). The second electrode 1408 can be positioned toward a central portion of the bottom surface of the CGM sensor 1402. The second electrode 1408 can be arranged in a third circle (e.g., concentric with the first circle of the adhesive pad 1404 and second circle of the first electrode 1406 and smaller).

In various embodiments, the CGM sensor 1402 can include a sensing cannula. The sensing cannula can extend from any portion of the bottom surface of the CGM sensor 1402 (e.g., from a center of the bottom surface). In various embodiments, the CGM sensor 1402 can be coupled to a user for multiple days—for example, for a period of time of 10 days or more.

FIG. 14 further shows a drug delivery device 1410. The drug delivery device 1410 can be an alternative implementation of the drug delivery device 102. FIG. 14 can show a top view of the drug delivery device 1410. The drug delivery device 1410 can include an adhesive pad 1412. The adhesive pad 1412 can be coupled to a bottom surface of the drug delivery device 1410. The drug delivery device 1410 can be attached to a user by the adhesive pad 1412 and intended to be used for a duration of time that is less than a duration of use of the CGM sensor 1402. For example, the duration of use of the drug delivery device 1410 can be approximately 3 to 4 days, after which the drug delivery device 1410 can be removed from the user (e.g., replaced by a next or subsequent drug delivery device 1410).

The drug delivery device 1410 can include an opening 1414. The CGM sensor 1402 can be positioned into the opening 1414. When positioned in the opening 1414, the CGM sensor 1402 can be coupled to the body of the user (e.g., the adhesive pad 1404 and the first and second electrodes 1406 and 1408 can contact the body of the user). Further, the CGM sensor 1402 can be electrically coupled to the drug delivery device 1410 when positioned in the opening 1414 to allow data from the CGM sensor 1402 to be provided to the drug delivery device 1410.

The drug delivery device 1410 can include an infusion cannula. Indicator 1416 shows a position or site of the infusion cannula (in phantom to indicate the site 1416 extends from the bottom surface of the drug delivery device 1410). In various embodiments, the CGM sensor 1402 can first be coupled to the body of a user. The drug delivery device 1410 can then be positioned over the CGM sensor 1402 such that the CGM sensor 1402 is positioned within the opening 1414. The drug delivery device 1410 can be positioned in any orientation relative to the CGM sensor 1402 such that the infusion site 1416 can be at any rotational position from a center of the CGM sensor 1402.

When the first drug delivery device 1410 has been used for its duration of use, it can be detached from the user without disrupting the position of the CGM sensor 1402. A second or subsequent drug delivery device 1410 can then be positioned over the CGM sensor 1402 and attached to the user. The second drug delivery device 1410 can be rotated relative to the former position of the first drug delivery device 1410 such that the infusion sites 1412 differ (e.g., vary by at least 90 degrees relative to a center of the CGM sensor 1402). In this way, the drug delivery system 1400 enables an unlimited number of orientations of the drug delivery device 1410 relative to the CGM sensor 1402 and therefore an unlimited number of possible infusion sites 1416 that can be changed over the course of use of the CGM sensor 1402 as multiple drug delivery device 1410 are used with the same CGM sensor 1402.

In various embodiments, the CGM sensor 1402 can include electronic components. In various embodiments, the drug delivery device 1410 can include only mechanical components. In various embodiments, the CGM sensor 1402 can include a controller component to control operation of the drug delivery device 1410.

Each of the drug delivery devices described herein can be a wearable or on-body drug delivery device or pump, such as an OmniPod (Insulet Corporation, Billerica, Mass., USA) device and/or any of the drug delivery devices described in U.S. Pat. Nos. 7,303,549; 7,144,384; 7,137,964; 6,960,192; 6,740,059; 6,699,218; 9,402,950; 7,771,412; 7,029,455; 6,740,05; and 6,656,159, each of which is incorporated herein by reference in its entirety. As such, each of the drug delivery devices disclosed herein can include one or more reservoirs or chambers configured to store a liquid drug and a drug delivery mechanism or component for extracting (e.g., pumping) the liquid drug out of the reservoir for delivery to a user. Further, each of the drug delivery devices disclosed herein can include one or more infusion cannulas for provided the stored liquid drug to the user over one or more doses and/or based on data provided by any of the sensors disclosed herein. In each of the disclosed embodiments, the sensor can be coupled to the drug delivery device in any manner (e.g., over a wired or wireless link) to allow the bidirectional flow of any data (e.g., control data, user data, etc.).

The following examples pertain to further embodiments.

Example 1 is a method comprising positioning a sensor on a body of a user, attaching the sensor to the body of a user with a first adhesive component positioned on a bottom surface of the sensor, positioning a drug delivery device over the sensor, the sensor positioned within a central opening of the drug delivery device, the drug delivery device covering all portions of the sensor except the bottom surface of the sensor attached to the user, the drug delivery device including a reservoir configured to store a liquid drug and a drug delivery component configured to extract the liquid drug from the reservoir for delivery to the user, attaching the drug delivery device to the body of the user with a second adhesive component positioned on a bottom surface of the drug delivery device, extending a sensing cannula from a center of the bottom surface of the sensor into the user, and extending an infusion cannula from a periphery of the bottom surface of the drug delivery device, the first infusion cannula spaced a predetermined distance from the sensing cannula.

Example 2 is an extension of Example 1 or any other example disclosed herein, wherein positioning the drug delivery device over the sensor further comprises positioning a base of the sensor within a recess of the drug delivery device, the recess of the drug delivery device surrounding the central opening of the drug delivery device.

Example 3 is an extension of Example 2 or any other example disclosed herein, wherein positioning the base of the sensor within the recess of the drug delivery device further comprises aligning the bottom surface of the sensor with the bottom surface of the drug delivery device.

Example 4 is an extension of Example 3 or any other example disclosed herein, wherein the bottom surface of the sensor is coplanar with the bottom surface of the drug delivery device.

Example 5 is an extension of Example 4 or any other example disclosed herein, wherein the sensor is a continuous glucose monitor (CGM) sensor and the liquid drug stored in the reservoir of the drug delivery device is insulin.

Example 6 is an extension of Example 5 or any other example disclosed herein, further comprising transmitting data indicative of glucose levels associated with the user from the CGM sensor to the drug delivery device.

Example 7 is an extension of Example 6 or any other example disclosed herein, further comprising wirelessly transmitting the data indicative of the glucose levels associated with the user from the drug delivery device to a controller component configured to control operation of the CGM sensor and the drug delivery device.

Example 8 is an extension of Example 5 or any other example disclosed herein, further comprising removing the drug delivery device after a first period of time while maintaining attachment of the CGM sensor to the body of the user, positioning a second drug delivery device over the CGM sensor, the CGM sensor positioned within a central opening of the second drug delivery device.

Example 9 is an extension of Example 8 or any other example disclosed herein, further comprising extending a second infusion cannula from a periphery of the bottom surface of the second drug delivery device, the second infusion cannula spaced the predetermined distance from the sensing cannula, the second infusion cannula spaced 180 degrees from a former position of the infusion cannula relative to a fixed position of the sensing cannula.

Example 10 is an extension of Example 9 or any other example disclosed herein, further comprising removing the second drug delivery device after a second period of time while maintaining attachment of the CGM sensor to the body of the user, positioning a third drug delivery device over the CGM sensor, the CGM sensor positioned within a central opening of the third drug delivery device.

Example 11 is an extension of Example 10 or any other example disclosed herein, further comprising extending a third infusion cannula from a periphery of the bottom surface of the third drug delivery device, the third infusion cannula spaced the predetermined distance from the sensing cannula, the third infusion cannula spaced 90 degrees from a former position of the second infusion cannula relative to the fixed position of the sensing cannula.

Example 12 is an extension of Example 11 or any other example disclosed herein, further comprising removing the third drug delivery device after a third period of time while maintaining attachment of the CGM sensor to the body of the user, positioning a fourth drug delivery device over the CGM sensor, the CGM sensor positioned within a central opening of the fourth drug delivery device.

Example 13 is an extension of Example 12 or any other example disclosed herein, further comprising extending a fourth infusion cannula from a periphery of the bottom surface of the fourth drug delivery device, the fourth infusion cannula spaced the predetermined distance from the sensing cannula, the fourth infusion cannula spaced 180 degrees from a former position of the third infusion cannula relative to the fixed position of the sensing cannula.

Example 14 is an extension of Example 13 or any other example disclosed herein, further comprising removing the fourth drug delivery device and the CGM sensor after a fourth period of time.

Example 15 is a method comprising attaching a bottom surface of a continuous glucose monitor (CGM) sensor to a body of a user, placing a first drug delivery device over the CGM sensor and positioning the CGM sensor within a central opening of the first drug delivery device, the first drug delivery device covering all of the CGM sensor other than the bottom surface of the CGM sensor, aligning the bottom surface of the CGM sensor to be coplanar with a bottom surface of the first drug, attaching the bottom surface of the first drug delivery device to the body of the user, extending a sensing cannula from a center of the bottom surface of the CGM sensor at a sensing site on the body of the user, extending a first infusion cannula from a periphery of the bottom surface of the first drug delivery device at a first infusion site on the body of the user, delivering a liquid drug to the first infusion site, the liquid drug stored in a reservoir of the first drug delivery device, detaching the first drug delivery device from the body of the user after a first period of time elapses while maintaining the sensing site, placing a second drug delivery device over the CGM sensor and positioning the CGM sensor within a central opening of the second drug delivery device, and extending a second infusion cannula from a periphery of a bottom surface of the second drug delivery device at a second infusion site on the body of the user, the second infusion site rotated at least 90 degrees from the first infusion site relative to the sensing site.

Example 16 is a drug delivery system comprising a sensor having a base component and a housing component positioned on the base component, the base component extending beyond a periphery of the housing component, a bottom surface of the base component configured to attach to a body of a user and a drug delivery device having a base component and a housing component positioned on the base component, the drug delivery device having a central opening in the base component and extending into the housing component configured to cover all portions of the sensor other than the bottom surface of the base component of the sensor, the drug delivery device having a recess surrounding the central opening, the recess configured to cover the base component of the sensor, the drug delivery device configured to store a liquid drug, wherein the bottom surface of the sensor is coplanar with the bottom surface of the drug delivery device when the sensor is positioned within the central opening of the drug delivery device, wherein the sensor includes a sensing cannula configured to extend from a center of the bottom surface of the base component of the sensor, wherein the drug delivery device includes an infusion cannula configured to extend from a periphery of the bottom surface of the drug delivery device, wherein the infusion cannula is configured to extend at a first position at any rotational position relative to the sensing cannula and spaced a first distance from the sensing cannula.

Example 17 is an extension of Example 16 or any other example disclosed herein, wherein the drug delivery device is configured to be positioned over the sensor in any rotational positional relative to the sensor.

Example 18 is an extension of Example 17 or any other example disclosed herein, wherein the drug delivery device and the sensor are communicatively coupled together when the drug delivery device is positioned over the sensor.

Example 19 is an extension of Example 18 or any other example disclosed herein, wherein the sensor is a continuous glucose monitor (CGM) senor and the liquid drug is insulin.

Example 20 is an extension of Example 19 or any other example disclosed herein, wherein the drug delivery device is configured to be removed after a first duration of use and replaced with a subsequent drug delivery device that is configured to be positioned over the CGM sensor.

Example 21 is an extension of Example 20 or any other example disclosed herein, wherein an infusion cannula of the subsequent drug delivery device is configured to extend from a second position at any rotational position relative to the sensing cannula, the second position different from the first position, and spaced the first distance from the sensing cannula.

Example 22 is an extension of Example 21 or any other example disclosed herein, wherein the second position is 180 degrees rotated from the first position relative to the sensing cannula.

Example 23 is an extension of Example 22 or any other example disclosed herein, wherein the second position is at least 90 degrees rotated from the first position relative to the sensing cannula.

Example 24 a method comprising attaching an adhesive pad having an incorporated continuous glucose monitor (CGM) sensor to a body of a user, coupling a CGM sensor configuration module to the adhesive pad and over the CGM sensor, engaging a user interface component positioned on the CGM sensor configuration module to configure operation of the CGM sensor, extending one or more sensing cannulas from a center of a bottom surface of the CGM sensor, removing the CGM sensor configuration module from the adhesive pad, coupling a first drug delivery device to the adhesive pad and over the CGM sensor in a first position, the first position one of a plurality of possible orientations relative to a positioning of the adhesive pad having the incorporated CGM sensor, extending a first infusion cannula from the first drug delivery device through a first opening in the adhesive pad to reach the body of the user, the first opening associated with the first position of the first drug delivery device, and infusing a liquid drug into the body of the user from the first drug delivery device over a first duration of use time period.

Example 25 is an extension of Example 24 or any other example disclosed herein, further comprising removing the first drug delivery device from the adhesive pad having the incorporated CGM sensor while maintaining the positioning of the adhesive pad having the incorporated CGM sensor, coupling a second drug delivery device to the adhesive pad and over the CGM sensor in second position, the second position one of the plurality of possible orientations relative to the positioning of the adhesive pad having the incorporated CGM sensor, the second position different from the first position, extending a second infusion cannula from the second drug delivery device through a second opening in the adhesive pad to reach the body of the user, the second opening associated with the second position of the second drug delivery device, and infusing the liquid drug into the body of the user from the second drug delivery device over a second duration of use time period.

Example 26 is an extension of Example 25 or any other example disclosed herein, wherein the second opening is rotated 180 degrees from the first opening relative to a position of the sensing cannula.

Example 27 is an extension of Example 26 or any other example disclosed herein, wherein the first and second openings are each positioned a same distance from the sensing cannula.

Example 28 is a drug delivery system comprising an adhesive pad having a plurality of openings configured to provide access to a body of a user, a bottom surface of the adhesive pad configured to be coupled to the body of the user, a continuous glucose monitor (CGM) sensor incorporated into the adhesive pad, the CGM sensor having one or more sensing cannulas extending from a bottom surface of the adhesive pad, a CGM sensor configuration module configured to be releasably attachable to the adhesive pad and positioned over the CGM sensor, the CGM sensor configuration module having a user interface component for configuring operation of the CGM sensor when the CGM sensor configuration module is attached to the adhesive pad and over the CGM sensor, a drug delivery device configured to be releasably attachable to the adhesive pad in one of a plurality of positions relative to a fixed position of the adhesive pad, the drug delivery device having an infusion cannula configured to extend through a first one of the plurality of openings of the adhesive pad to reach the body of the user, the drug delivery device configured to be detached from the adhesive pad after a first period of time without disrupting a positioning of the one or more sensing cannulas and to be replaced by a second drug delivery device.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

The invention claimed is:

1. A method, comprising:
    positioning a sensor on a body of a user;
    attaching the sensor to the body of a user with a first adhesive component positioned on a bottom surface of the sensor;
    positioning a drug delivery device over the sensor, the sensor positioned within a central opening of the drug delivery device, the drug delivery device covering all portions of the sensor except the bottom surface of the sensor attached to the user, the drug delivery device including a reservoir configured to store a liquid drug and a drug delivery component configured to extract the liquid drug from the reservoir for delivery to the user;
    attaching the drug delivery device to the body of the user with a second adhesive component positioned on a bottom surface of the drug delivery device;
    extending a sensing cannula from a center of the bottom surface of the sensor into the user; and
    extending an infusion cannula from a periphery of the bottom surface of the drug delivery device, the infusion cannula spaced a predetermined distance from the sensing cannula.

2. The method of claim 1, wherein positioning the drug delivery device over the sensor further comprises:
    positioning a base of the sensor within a recess of the drug delivery device.

3. The method of claim 2, wherein positioning the base of the sensor within the recess of the drug delivery device further comprises:
    aligning the bottom surface of the sensor with the bottom surface of the drug delivery device.

4. The method of claim 1, wherein the bottom surface of the sensor is coplanar with the bottom surface of the drug delivery device.

5. The method of claim 1, wherein the sensor is a continuous glucose monitor (CGM) sensor and the liquid drug stored in the reservoir of the drug delivery device is insulin.

6. The method of claim 5, further comprising;
    transmitting data indicative of glucose levels associated with the user from the CGM sensor to the drug delivery device.

7. The method of claim 6, further comprising;
    wirelessly transmitting the data indicative of the glucose levels associated with the user from the drug delivery device to a controller component configured to control operation of the CGM sensor and the drug delivery device.

8. The method of claim 5, further comprising;
    removing the drug delivery device after a first period of time while maintaining attachment of the CGM sensor to the body of the user; and
    positioning a second drug delivery device over the CGM sensor, the CGM sensor positioned within a central opening of the second drug delivery device.

9. The method of claim 8, further comprising:
    extending a second infusion cannula from a periphery of the bottom surface of the second drug delivery device, wherein the second infusion cannula is spaced the predetermined distance from the sensing cannula, and the second infusion cannula is spaced 180 degrees from a former position of the infusion cannula relative to a fixed position of the sensing cannula.

10. The method of claim 9, further comprising:
    removing the second drug delivery device after a second period of time while maintaining attachment of the CGM sensor to the body of the user; and
    positioning a third drug delivery device over the CGM sensor, the CGM sensor positioned within a central opening of the third drug delivery device.

11. The method of claim 10, further comprising:
    extending a third infusion cannula from a periphery of the bottom surface of the third drug delivery device, wherein the third infusion cannula is spaced the predetermined distance from the sensing cannula, and the third infusion cannula is spaced 90 degrees from a former position of the second infusion cannula relative to the fixed position of the sensing cannula.

12. The method of claim 11, further comprising:
removing the third drug delivery device after a third period of time while maintaining attachment of the CGM sensor to the body of the user; and
positioning a fourth drug delivery device over the CGM sensor, the CGM sensor positioned within a central opening of the fourth drug delivery device.

13. The method of claim 12, further comprising:
extending a fourth infusion cannula from a periphery of the bottom surface of the fourth drug delivery device, wherein the fourth infusion cannula is spaced the predetermined distance from the sensing cannula, and the fourth infusion cannula is spaced 180 degrees from a former position of the third infusion cannula relative to the fixed position of the sensing cannula.

14. The method of claim 13, further comprising:
removing the fourth drug delivery device and the CGM sensor after a fourth period of time.

15. A method, comprising:
attaching a bottom surface of a continuous glucose monitor (CGM) sensor to a body of a user;
placing a first drug delivery device over the CGM sensor and positioning the CGM sensor within a central opening of the first drug delivery device, the first drug delivery device covering all of the CGM sensor other than the bottom surface of the CGM sensor;
aligning the bottom surface of the CGM sensor to be coplanar with a bottom surface of the first drug;
attaching the bottom surface of the first drug delivery device to the body of the user;
extending a sensing cannula from a center of the bottom surface of the CGM sensor at a sensing site on the body of the user;
extending a first infusion cannula from a periphery of the bottom surface of the first drug delivery device at a first infusion site on the body of the user;
delivering a liquid drug to the first infusion site, the liquid drug stored in a reservoir of the first drug delivery device;
detaching the first drug delivery device from the body of the user after a first period of time elapses while maintaining the sensing site;
placing a second drug delivery device over the CGM sensor and positioning the CGM sensor within a central opening of the second drug delivery device; and
extending a second infusion cannula from a periphery of a bottom surface of the second drug delivery device at a second infusion site on the body of the user, the second infusion site rotated at least 90 degrees from the first infusion site relative to the sensing site.

16. A drug delivery system, comprising:
a sensor having a base component and a housing component positioned on the base component, the base component extending beyond a periphery of the housing component, a bottom surface of the base component configured to attach to a body of a user; and
a drug delivery device having a base component and a housing component positioned on the base component, the drug delivery device having a central opening in the base component and extending into the housing component configured to cover all portions of the sensor other than the bottom surface of the base component of the sensor, the drug delivery device having a recess surrounding the central opening, the recess configured to cover the base component of the sensor, the drug delivery device configured to store a liquid drug,
wherein the bottom surface of the sensor is coplanar with the bottom surface of the drug delivery device when the sensor is positioned within the central opening of the drug delivery device,
wherein the sensor includes a sensing cannula configured to extend from a center of the bottom surface of the base component of the sensor,
wherein the drug delivery device includes an infusion cannula configured to extend from a periphery of the bottom surface of the drug delivery device, wherein the infusion cannula is configured to extend at a first position at any rotational position relative to the sensing cannula and spaced a first distance from the sensing cannula.

17. The drug delivery system of claim 16, wherein the drug delivery device is configured to be positioned over the sensor in any rotational position relative to the sensor.

18. The drug delivery device of claim 17, wherein the drug delivery device and the sensor are communicatively coupled together when the drug delivery device is positioned over the sensor.

19. The drug delivery device of claim 18, wherein the sensor is a continuous glucose monitor (CGM) sensor and the liquid drug is insulin.

20. The drug delivery device of claim 19, wherein the drug delivery device is configured to be removed after a first duration of use and replaced with a subsequent drug delivery device that is configured to be positioned over the CGM sensor.

21. The drug delivery device of claim 20, wherein an infusion cannula of the subsequent drug delivery device is configured to extend from a second position at any rotational position relative to the sensing cannula, the second position different from the first position, and spaced the first distance from the sensing cannula.

22. The drug delivery device of claim 21, wherein the second position is 180 degrees rotated from the first position relative to the sensing cannula.

23. The drug delivery device of claim 21, wherein the second position is at least 90 degrees rotated from the first position relative to the sensing cannula.

* * * * *